United States Patent [19]

Hasson

[11] Patent Number: 5,562,680
[45] Date of Patent: Oct. 8, 1996

[54] APPARATUS FOR ASSISTING THE PERFORMANCE OF PELVIC ENDOSCOPIC PROCEDURES

[76] Inventor: Harrith M. Hasson, 2043 N. Sedgwick, Chicago, Ill. 60614

[21] Appl. No.: 406,796

[22] Filed: Mar. 20, 1995

Related U.S. Application Data

[63] Continuation of Ser. No. 816,667, Jan. 3, 1992, abandoned.

[51] Int. Cl.$^6$ .............................. A61B 17/42; A61B 17/46
[52] U.S. Cl. ............................................................. 606/119
[58] Field of Search ................................... 128/762, 778; 600/6; 604/1; 606/1, 119, 108, 190, 191, 193, 205–209

[56] References Cited

U.S. PATENT DOCUMENTS

| | | | |
|---|---|---|---|
| 2,977,958 | 4/1961 | Seiger | 606/205 |
| 3,877,464 | 4/1975 | Vermes | 604/1 |
| 4,000,743 | 1/1977 | Weaver | 606/119 |
| 4,175,560 | 11/1979 | Knoll | 604/1 |
| 4,393,872 | 7/1983 | Reznik et al. | 606/206 |
| 4,432,352 | 2/1984 | Wineland | 606/208 |
| 4,585,438 | 4/1986 | Makler | 604/106 |
| 4,997,419 | 3/1991 | Lakatos et al. | 606/190 |
| 5,037,430 | 8/1991 | Masson | 606/119 |
| 5,059,198 | 10/1991 | Gimpelson | 606/119 |
| 5,104,377 | 4/1992 | Levine | 606/193 |

FOREIGN PATENT DOCUMENTS 0369334  1/1907  France ..................................... 604/11

*Primary Examiner*—Michael H. Thaler
*Assistant Examiner*—Glenn Dawson
*Attorney, Agent, or Firm*—Wood, Phillips, VanSanten, Clark & Mortimer

[57] ABSTRACT

An apparatus for assisting the performance of laparoscopic pelvic procedures. The apparatus has a first structure for engaging a uterus to effect stabilization thereof and a second structure for holding a spacing material such as a resilient moisture absorbent material into the vaginal fornix. The first and second structures are cooperatively engaged to allow the resilient moisture absorbent material held by the second structure to be selectively movably positioned relative to a uterus which is engaged by the first structure. The invention further contemplates a method of assisting the performance of laparoscopic pelvic procedures, which method consists of the steps of: providing a structure to grasp the uterine cervix; grasping the uterus with the structure to stabilize the position thereof; providing an elongate rod with a proximal end and a distal end; connecting the elongate rod to the cervix grasping structure for movement relative thereto; attaching the resilient material at the distal end of the elongate rod; and manipulating the proximal end of the elongate rod to change the position of the elongate rod relative to the uterine grasping structure and position the resilient material at the distal end of the elongate rod where desired in the vicinity of the uterine cervix.

16 Claims, 2 Drawing Sheets

APPARATUS FOR ASSISTING THE PERFORMANCE OF PELVIC ENDOSCOPIC PROCEDURES

This application is a continuation of application Ser. No. 07/816,667, filed Jan. 3, 1992, now abandoned.

BACKGROUND OF THE INVENTION

1. Field of the Invention

This invention relates to pelvic endoscopic surgical procedures and, more particularly, to an apparatus that can be used to simultaneously support the uterus and distend the vagina through the placement of resilient moisture absorbent material around the cervix. This facilitates identification of the vaginal apex and prevents vaginal collapse around the cervix, to thereby minimize escape of gas used to distend the abdominal cavity, as during the performance of a laparoscopic hysterectomy.

2. Background Art

It is estimated that in the last year approximately 600,000 hysterectomies were performed. Hysterectomies are conventionally performed either through the abdomen or the vagina.

The abdominal hysterectomy is performed by making an incision in the abdomen which is large enough to access, sever and remove the uterus with or without the fallopian tubes and ovaries. The procedure is completed by stitching closed the vaginal opening which is penetrated by the cuff of the cervix. The abdominal hysterectomy is desirable in that it can be performed on virtually all patients. The principal drawbacks associated with this type of procedure are that the patient experiences pain from the incision and healing may require relatively lengthy hospitalization.

The vaginal hysterectomy is performed through the vaginal opening by progressively cutting out and removing the uterus, fallopian tubes and ovaries. Performance of the hysterectomy by the vaginal technique is preferred over the abdominal technique principally because the patient remains unscarred and may require only a short hospital stay.

The vaginal technique has several limitations however. First of all, performance of the vaginal hysterectomy requires a relaxed vaginal opening, to permit access to the cervix and beyond. Therefore, not all women are candidates for laparoscopic hysterectomies, particularly those who have not already borne children.

Recently, a laparoscopic technique has been described through which the uterus is removed through the vagina. This technique utilizes a telescope, video camera and monitor and various other special instruments introduced into the abdomen through small incisions.

The principal drawback with vaginal hysterectomies is the inherent dangers associated with this type of operation due to a) loss of depth perception from a video screen as well as the loss of palpatory information otherwise available with an open abdomen and b) the limited points of access through which instruments can be directed and utilized. The region of the uterus which is severed during a hysterectomy is in close proximity to the rectum, bladder and other vital organs which, if inadvertently cut or severed, could cause severe internal injury or even death. The operation itself is a very delicate one requiring the disconnection of the ovaries, the ligaments supporting the uterus, etc. in a very precise fashion. Accordingly, during the laparoscopic procedure, it is necessary that all internal organs be positively identifiable at all times during the surgery.

To provide the necessary visibility during the performance of the laparoscopic hysterectomy, it is important to distend the abdominal cavity by the introduction of a gas to enlarge the working area. However, once a vaginal incision is made, the system is no longer closed and the gas escapes. This results in a confined working area. Blood accumulation therein virtually destroys what little visibility remains. To continue the surgery under these circumstances, special tools are required to open the vaginal cuff. To effectively do this, it is important that the uterus be supported in a proper orientation, which may require even additional instruments.

To overcome these problems, it is known to provide rods with sponges on the ends thereof to block the escape of gas after an incision is made into the vaginal apex during laparoscopic hysterectomy. Commonly, one or a plurality or the rods are directed through the vagina into the vicinity of the cervical cuff. The principal difficulty with this conventional technique is that the surgeon is required to blindly direct the sponge into position. A misdirected rod could itself cause a rupture or difficulty in identifying the vaginal apex with possible subsequent entry into the bladder or rectum.

Additionally, it is difficult and may be virtually impossible for the surgeon to control the positioning of all of the separate instruments that are directed through the vaginal opening to distend the vaginal apex and elevate the uterus at the same time during the hysterectomy. Not only is there the potential for interference between the many instruments, but there is also increased likelihood that the surgeon may confuse the identity of the instruments with again potentially dire consequences.

SUMMARY OF THE INVENTION

The present invention is specifically directed to overcoming the above-enumerated problems in a novel and simple manner.

More particularly, the invention comprehends an apparatus for assisting the performance of pelvic laparoscopic procedures, for example, a laparoscopic hysterectomy. The apparatus has a first structure for engaging a uterus/cervix to effect stabilization thereof and a second structure for holding a resilient moisture absorbent material. The first and second structures are cooperatively engaged to allow the resilient moisture absorbent material held by the second structure to be selectively movably positioned relative to a cervix which is engaged by the first structure.

Because the first structure uses the uterus/cervix as a foundation, the second structure can be positively guided relative to the cervix and first structure thereon to consistently position and hold a resilient moisture absorbent material, such as a sponge, where desired, particularly in the vaginal cuff surrounding the cervix.

In one form, the first and second structures are connected together for pivoting movement relative to each other about a first axis.

To provide a further degree of freedom for the second structure, the second structure can be movable in a translatory path relative to the first structure along a line that is transverse to the first axis.

In another form of the invention, there is a third structure for holding a resilient moisture absorbent material that cooperates with at least one of the first and second structures to allow the moisture absorbent material thereon to be controllably directed to a position wherein it blocks escape of gas from an abdomen during the performance of a laparoscopic hysterectomy. The third structure is, in a preferred form, connected to the first structure for both relative pivoting and translatory movement.

While the first structure may take any of a number of different forms, it is, in one preferred form of the invention, a tenaculum having legs pivotably joined so as to operate as a scissors. The second and third structures can be mounted to either of the legs of the tenaculum for pivoting and/or translatory movement relative to that leg.

The invention contemplates that the conventional type tenaculum or other cervical clamping mechanisms could be integrally constructed with, or retrofit to include structure to support the first and second structures for relative movement. In one form, a block is provided on the tenaculum or other clamping structure and is movably attached thereto by providing joinable halves. One or more sleeves are pivotably attached to the block and accept the second and third structures which, in a preferred form, are elongate rods slidable within the sleeve in a direction lengthwise of the rods.

In one form of the invention, each elongate rod or other suitable structure performing the function of the rods, can be fixed relative to the sleeve which in turn can be fixed relative to the block. A tenaculum or other suitable clamping structure, serves as a solid foundation for the rod(s) once clamped to the cervix. The moisture absorbent material is thus positively held in its proper position relative to the cervix. The surgeon is not required to manipulate a plurality of instruments as required when using prior art structures. At the same time, the first, second and third structures cooperate to allow presetting of the apparatus so that the resilient moisture absorbent material is predictably positioned, thereby avoiding the risk of injury potentially caused by a misdirected part of an instrument.

To add further versatility to the inventive device, a support can be provided at the free end of a tenaculum or other clamping structure to maintain the uterus in optimal positions for the performance of the hysterectomy. Typically, the tenaculum has cooperating jaws. By providing an extension thereon, in the form of a rod, uterine support can be provided. The extension can be custom fitted to a particular patient or made malleable so that the surgeon can reconfigure the shape of the tenaculum on site. The invention also contemplates different, interchangeable, uterine support rods provided in various lengths i.e. 5 to 10 cm in length and exemplary thicknesses of 3, 5 and 7 mm so as to custom fit individual uteri. The uterine support rods are preferably made of malleable material to be bendable according to the position of the uterus, i.e. anteflexed, straight or retroverted. Uterine support rods are removably attachable securely to the distal end of one tenaculum jaw.

The invention further contemplates a method of assisting the performance of laparoscopic pelvic procedures, which method consists of the steps of: providing a structure to grasp the cervix; grasping the cervix with the structure to stabilize the position thereof; providing an elongate rod with a proximal end and a distal end; connecting the elongate rod to the cervix grasping structure for movement relative thereto; attaching the resilient material at the distal end of the elongate rod; and manipulating the proximal end of the elongate rod to change the position of the elongate rod relative to the cervical grasping structure and position the resilient material at the distal end of the elongate rod where desired in the vicinity of the cervix.

A second elongate rod could be provided and manipulated in similar fashion.

To make the inventive apparatus more versatile, provision can be made to hold different sizes of resilient moisture absorbent material. The surgeon can thus select the size of material required and readily effect connection thereof.

DETAILED DESCRIPTION OF THE DRAWINGS

In FIGS. 1–8, a preferred form of apparatus for assisting the performance of intrauterine procedures, according to the present invention, is shown at 10. The apparatus 10 consists of a tenaculum 12 and elongate rods 14, 16 supported to the tenaculum 12 for guided movement relative thereto. The distal ends 18, 20 of the rods 14, 16 are designed, as described in greater detail below, to releasably accept a resilient, preferably moisture absorbent material, such as gauze or other type of sponge material. Before the details of the apparatus 10 are described, the general purpose of the apparatus 10 will be explained with reference to FIG. 6.

Figure 6:
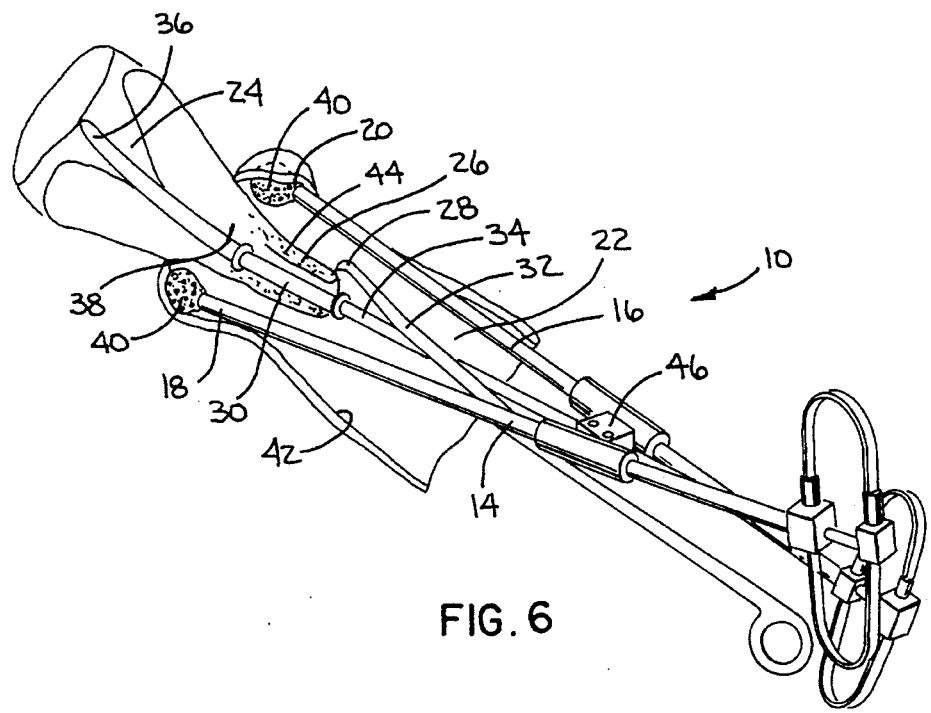
FIG. 6 is perspective view of the apparatus of FIGS. 1 and 2 operatively positioned within a vagina, cervix and uterus.
Figure 7:
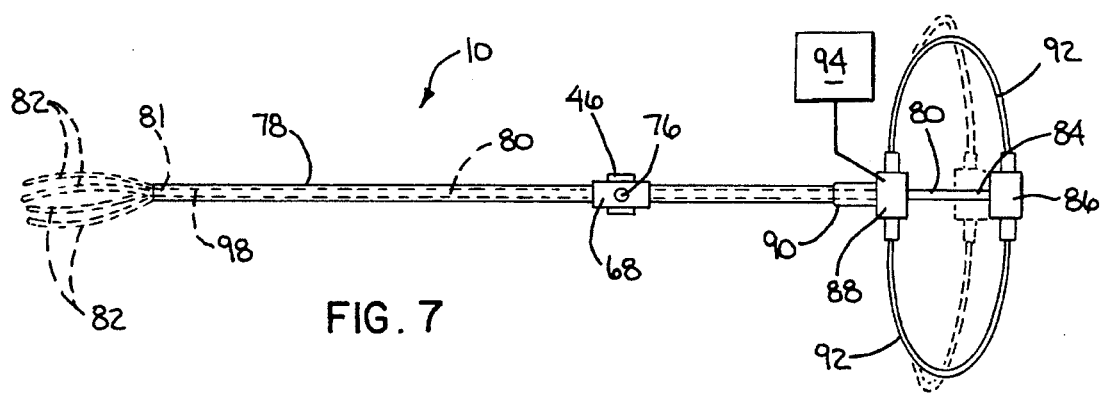
FIG. 7 is a side elevation view of one of the rods on the inventive apparatus shown reconfigured to attach/release moisture absorbent material from the distal end thereof.
Figure 8:
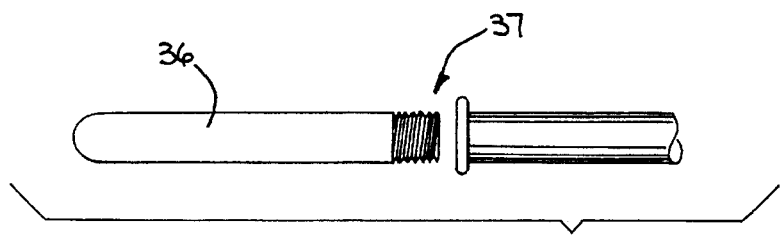
FIG. 8 is an enlarged, side elevation view of the end o f the tenaculum on the inventive apparatus and showing a structure for allowing interchange of different uterine support ends/extensions.

In FIG. 6, a vagina is shown at 22 through which internal access can be gained to a uterus 24, as for the performance of a hysterectomy. The cervix 26 is grasped between the distal ends 28, 30 of a pair of jaws 32, 34, respectively, on the tenaculum 12. The distal end 30 of the jaw 34 has an extension 36 which projects into the uterine cavity 38 to support the uterus in a desired working orientation. Extension 36 is integrally formed with the jaw 34 or, in a preferred form, is a separate element that can be removably attached as by a threaded connection 37 (FIG. 8) Other releasable attachment means are also contemplated by the invention. In this way, different extensions 36 of various lengths and thickness can be selectively attached to jaw 34 for custom fitting. With the tenaculum 12 in the FIG. 6 orientation, the cervix 26 is stabilized and the apparatus 10 positively held relative thereto in its operative position.

The distal ends 18, 20 of the rods 14, 16 each carry a spacing material which is a moisture absorbent material 40, generally in the nature of a sponge, gauze, or the like. To prevent escape of gas from the abdomen during a surgical procedure, the moisture absorbent material is urged between the interior vaginal wall 42 and external cervical wall 44 at posterior and anterior vaginal locations.

One of the principal objectives of the present invention is to controllably situate and maintain the moisture absorbent material 40 sealingly between the cervix 26 and vaginal wall 42 prior to incising the vaginal wall from above during the performance of a hysterectomy. The tenaculum 12 provides a rigid support for the rods 14, 16 so that the surgeon not only consistently guides the sponges 40 into place, but is not required to manipulate the rods 14, 16 after attachment of the tenaculum 12 to the cervix 26.

Figure 3:
FIG. 3 is an enlarged, perspective view of a mounting block for the rods carrying the moisture absorbent material.
Figure 4:
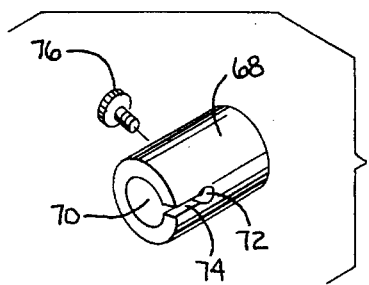
FIG. 4 is a perspective view of a sleeve which is mountable to the block in FIG. 3 and cooperates with an elongate rod to guide translatory movement thereof relative to the block.
Figure 5:
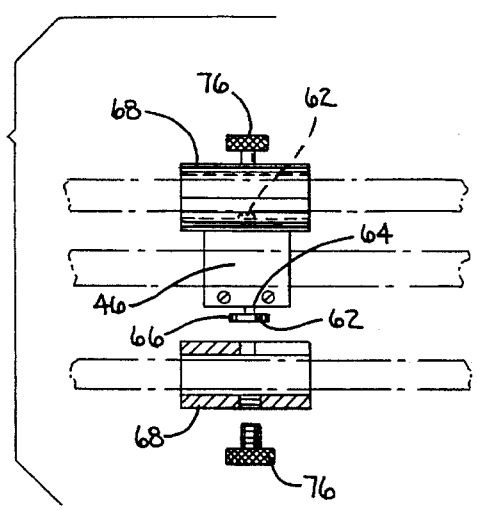
FIG. 5 is a fragmentary plan view showing the mounting block with one of the rod guiding sleeves mounted thereon and the other separated therefrom.

The present invention contemplates movement of elongate rods, 14, 16 relative to the tenaculum 12 so that one apparatus configuration is able to accommodate virtually all patients. More particularly, each of the rods 14, 16 is attached to the tenaculum 12 so as to be able to pivot and translate relative thereto. To accomplish this, a block 46 is provided on one of two legs 48, 50, which are joined by a pin 52 for operation in the same manner as a conventional scissors. The block 46 can be integrally formed with the leg 48 or, as depicted in FIG. 3, can be constructed in two pieces, so as to be retrofit to a tenaculum 12. In FIG. 3, the block has joinable halves 54, 56 which, when operatively assembled, define a through bore 58 having a cross section matched to that of the leg 48. Screws 60 hold the block halves 54, 56 together to thereby captively hold the block 46 onto the leg 48.

A pivot pin 62 projects laterally from each side of the block 46. Each pin 62 has a stem 64 which is anchored to the block 46 and an enlarged head 66 at the free end of the stem 64.

Each pivot pin 62 carries a guide sleeve 68 having a cylindrical configuration and a through bore 70. Each guide sleeve 68 has a pivot opening 72 for the stem 64 on one of the pivot pins 62 and an entry slot 74 having a width slightly less than the diameter of the stem 64 and the pivot opening 72. To effect assembly of the guide sleeve 68, the guide sleeve 68 is positioned to align the entry slot 74 with the stem 64 which is forced therethrough by a slight deformation of the guide sleeve 68 until the stem 64 resides in the pivot opening 72. The guide sleeve 68 can be made of any material that both permits the modicum of deformation necessary to allow seating of the pin 62 in the pivot opening 72 and has sufficient memory to recapture its undeformed state so that the sleeve 68 does not escape from the pin 62.

The rods 14, 16 each have an outside diameter slightly less than the diameter of the through bore 70 on the guide sleeves 68. With the rods 14, 16 extended into the sleeves 68, the rods 14, 16 can rotate with the sleeve 68 about axes defined by the pins 62 and are translatable relative thereto transversely to the pin axes.

To fix the position of the rods 14, 16 relative to the sleeves 68 and in turn the sleeves 68 relative to the block 46, set screws 76 are provided at diametrically opposite locations to the pivot openings 72 on the sleeves 68. By tightening the set screws 76, the rods 14, 16 are pressed against the pivot pin heads 66 so that the position of the sleeves 68 and rods 14, 16, relative to the block 46, is frictionally held.

It should be understood that the invention contemplates all different variations of mechanism that allow translatory and pivoting movement of the rods 14, 16 relative to the block 46. The structure shown herein is only exemplary.

Each of the rods 14, 16 is identical. Each rod 14, 16 has a guide casing 78 for an internal control rod 80. The rod 80 has at its distal end 81 a plurality of claws 82 which are normally biased outwardly and cooperatively define a cage-type receptacle for the moisture absorbent material 40. The proximal end 84 of the rod 80 has a spring mounting block 86 thereon. A similar mounting block 88 is provided on the proximal end 90 of the guide casing 78. An elliptical leaf-type spring 92 extends through the blocks 86, 88. By moving the block 86 toward the block 88, the minor axis of the elliptical spring 92 is collapsed which causes the claws 82 to project out of the distal end 81 of the guide casing 78. In so doing, the claws 82 spring radially outwardly to define a receptacle for the moisture absorbent material 40. This movement of the spring 92 is accomplished readily by grasping the mechanism in the manner of a syringe and pressing the block 86 with the thumb in the direction of the block 88. If it is desired to keep the claws 88 in the FIG. 7 configuration, the rod 80 can be locked as by a mechanism shown schematically at 94 in FIG. 7. A suitable structure is shown as a set screw 96 in FIG. 1.

To put the moisture absorbent material 40 in place, it is directed into the receptacle defined by the claws 82. By releasing the force on the spring 92, the spring 92 bends back towards its undeformed state, drawing the rod 80 from left to right in FIG. 7 and in so doing forcing the claws 82 into the internal opening 98 defined by the casing 78. This causes the claws 82 to collapse and thereby squeeze the moisture absorbent material therebetween.

To operate the device, the surgeon can, with conventional instruments, measure the depth of the uterus and ascertain the optimal position for the moisture absorbing material. The preset instrument 10 is directed through the cervical opening into the uterine cavity so that the tenaculum extension 36 fully supports the uterine cavity 38. The tenaculum 12 is then locked to the cervix 26 by closing the jaws 32, 34 thereon by urging finger rings 100, 102 towards each other in the same manner as using a scissors. A ratchet mechanism at 104 holds the jaws 32, 34 on the cervix 26 with the desired gripping force. The rods 14, 16 are then preset at a desired angle and longitudinally positioned relative to the tenaculum 12 to provide the desired amount of penetration into the vagina 22. This firmly holds the moisture absorbent material 40 in a desired position, shown in FIG. 6. Once the tenaculum 12 is locked in place, the surgeon need not monitor the orientation of the rods 14, 16, as the same is fixed. It can be seen that the apparatus 10 is functional as a unitary assembly that is adjustable to virtually all patients.

Figure 1:
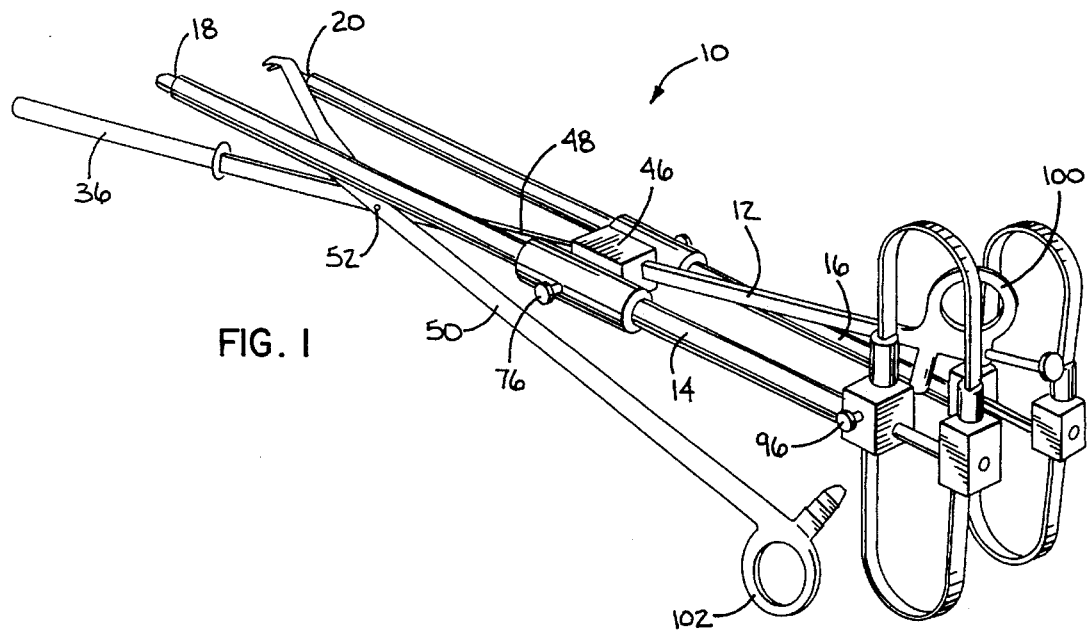
FIG. 1 is a perspective view of an apparatus for assisting the performance of laparoscopic uterine procedures, according to the present invention, and consisting of a tenaculum and two associated rods for carrying resilient moisture absorbent material.
Figure 2:
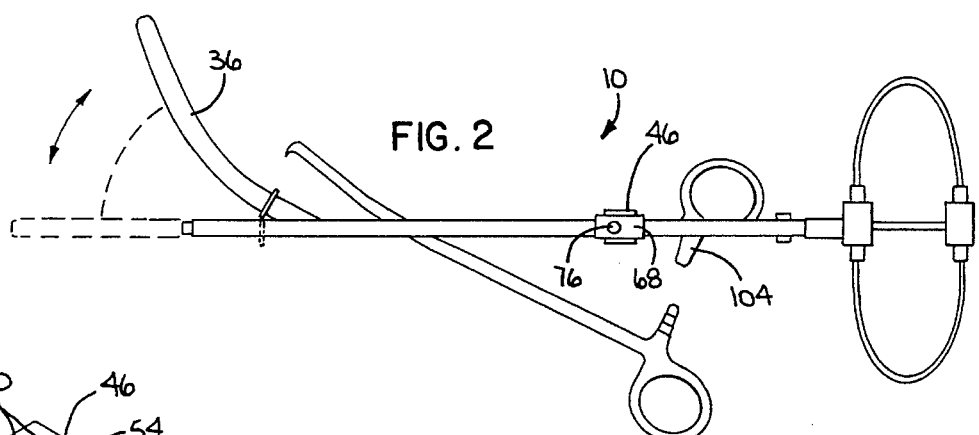
FIG. 2 is a side elevation of the apparatus in FIG. 1 and showing two different positions for a uterine support rod mounted or securably attached on one of the jaws of the tenaculum.

To make the apparatus 10 more universal, the extensions 36 are made malleable and of different lengths and thicknesses so that they can be custom fitted and bent as desired to effectively support the uterus 24. In FIG. 1, the extension 36 is shown to be straight, whereas in FIG. 2, in solid lines, it is curved upwardly at approximately a 45° angle.

It can be seen that the present invention affords support for the uterus 24 and positively holds the moisture absorbent material 40 in place in the vaginal fornix so as to identify the anatomic structures clearly, thereby preventing injury and also preventing escape of gas from the abdomen upon the vagina being cut, as during a hysterectomy. The spacing between the cervix 26 and vaginal wall 42 is maintained by the moisture absorbent material 40 which further facilitates the performance of laparoscopic surgical procedures.

The foregoing disclosure of specific embodiments is intended to be illustrative of the broad concepts comprehended by the invention.

I claim:

1. An apparatus for assisting the performance of intrauterine procedures, said apparatus comprising:

first means for engaging a cervix to effect stabilization thereof;

second means for holding a spacing material;

a first resilient spacing material held by the second means;

means for supporting the second means on the first means for controlled guided movement of the second means relative to the first means; and means cooperating between the first and second means for holding said second means in a selected orientation relative to said first means so that the resilient spacing material held by the second means can be selectively positioned relative to a cervix which is engaged by the first means.

2. The apparatus for assisting the performance of intrauterine procedures according to claim 1 wherein the cooperating means includes means connecting the second means to the first means for pivoting movement relative to the first means about a first axis.

3. The apparatus for assisting the performance of intrauterine procedures according to claim 2 wherein the cooperating means includes means connecting the second means to the first means for translating movement of the second means relative to the first means along a line transverse to the first axis.

4. The apparatus for assisting the performance of intrauterine procedures according to claim 1 including a second resilient spacing material and third means for holding the second resilient spacing material and cooperating means on the third means and at least one of the first and second means for allowing the second resilient spacing material held by the third means to be selectively movably positioned relative to a cervix which is engaged by the first means.

5. The apparatus for assisting the performance of intrauterine procedures according to claim 4 wherein the cooperating means on the third means and at least one of the first and second means includes means connecting the third means to the first means for pivoting movement relative to the first means about a second axis.

6. The apparatus for assisting the performance of intrauterine procedures according to claim 5 wherein the cooperating means on the third means and at least one of the first and second means includes means connecting the third means to the first means for translatory movement of the third means relative to the first means along a line that is transverse to the second axis.

7. The apparatus for assisting the performance of intrauterine procedures according to claim 1 wherein the first means is a tenaculum having pivotably joined legs and the means cooperating between the first and second means includes a mounting block on one of the first and second tenaculum legs and means for pivotably connecting the second means to the block for movement relative to the block.

8. An apparatus for assisting the performance of intrauterine procedures, said apparatus comprising:

first means for engaging a cervix to effect stabilization thereof;

a spacing material;

second means for holding the spacing material; and means for supporting the second means on the first means for controlled guided movement relative to the first means and allowing the spacing material held by the second means to be selectively movably positioned relative to a cervix which is engaged by the first means, said first means being a tenaculum having pivotably jointed first and second legs and the support means includes a mounting block on one of the first and second legs and means for pivotably connecting the second means to the mounting block for movement relative to the mounting block, the tenaculum legs each having a jaw, and further comprising a deformable extension beyond the jaw on one of the tenaculum legs to support a uterus in a desired orientation with a cervix being held by the jaws of the tenaculum.

9. An apparatus for assisting the performance of intrauterine procedures, said apparatus comprising:

first means for engaging a cervix to effect stabilization thereof;

a resilient moisture absorbent material;

second means including expandable jaw means holding said resilient moisture absorbent material;

cooperating means on the first and second means for allowing the second means and said resilient moisture absorbent material held by the jaw means to be selectively guidingly moved relative to the first means and a cervix which is engaged by the first means; and means cooperating between the first and second means for selectively holding the position of the second means relative to the first means.

10. An apparatus for assisting the performance of intrauterine procedures, said apparatus comprising;

first means for engaging a cervix to effect stabilization thereof;

a first elongate rod;

means connecting the first elongate rod to the first means for controlled guided movement of the first elongate rod relative to the first means and for holding said first elongate rod in a selected orientation relative to said first means, said first elongate rod having a proximal end and a distal end, movement of said distal end being permitted by the connecting means to allow the distal end of the first elongate rod to be selectively positioned in the vicinity of a cervix which is engaged by the first means from a location remote from the cervix, wherein the connecting means includes means connecting the elongate rod for pivoting movement relative to the first means about a first axis; and a second elongate rod and means connecting the second elongate rod to the first means for selective movement of the second elongate rod relative to the first means, said second elongate rod having a proximal end and a distal end, movement of said distal end of the second elongate rod being permitted to allow the distal end of the second elongate rod to be selectively positioned in the vicinity of the cervix from a location remote from the cervix.

11. The apparatus for assisting the performance of intrauterine procedures according to claim 10 wherein the connecting means for the first and second elongate rods connects the first and second elongate rods for pivoting movement relative to the first means about parallel axes.

12. An apparatus for assisting the performance of intrauterine procedures, said apparatus comprising:

first means for engaging a cervix to effect stabilization thereof;

a first elongate rod;

means connecting the first elongate rod to the first means for selective movement of the first elongate rod relative to the first means, said first elongate rod having a proximal end and a distal end, movement of said distal end being permitted by the connecting means to allow the distal end of the first elongate rod to be selectively positioned in the vicinity of a cervix from a location remote from a cervix, said connecting means including means connecting the elongate rod for pivoting movement relative to the first means about a first axis; and a second elongate rod and means connecting the second elongate rod to the first means for selective movement of the second elongate rod relative to the first means around a second axis, said second elongate rod having a proximal end and a distal end, movement of said distal end of the second elongate rod being permitted to allow the distal end of the second elongate rod to be selectively positioned in the vicinity of a cervix from a location remote from a cervix, wherein the connecting means for the first and second elongate rods includes a block, the pivot axes for the first and second elongate rods are coincident and extend through the block and there are first and second guide sleeves attached pivotably to the block, said first and second guide sleeves guiding translatory movement of the first and second elongate rods respectively relative thereto and the block.

13. The apparatus for assisting the performance of intrauterine procedures according to claim 12 wherein each said guide sleeve has a through bore for slidably accepting its respective elongate rod and there are locking means for fixing the position of at least one of the elongate rods relative to its respective guide sleeve.

14. The apparatus for assisting the performance of intrauterine procedures according to claim 13 wherein the locking means includes means for fixing the guide sleeve accepting the one of the elongate rods against pivoting relative to the block.

15. A method of assisting the performance of intrauterine procedures, said method comprising the steps of:

providing a structure to grasp a cervix;

grasping the cervix with the structure to stabilize the position thereof;

providing an elongate rod with a proximal end and distal end;

connecting the elongate rod to the cervix grasping structure;

attaching a resilient material at the distal end of the elongate rod;

manipulating the proximal end of the elongate rod to change the position of the elongate rod relative to the cervix grasping structure and position the resilient material at the distal end of the elongate rod where desired on the outside of the cervix; and releasably fixing said elongate rod to the cervix grasping structure in a selected orientation relative thereto to hold said resilient material in the desired position.

16. The method of assisting the performance of intrauterine procedures according to claim 15, said method further including the steps of providing a second elongate rod with a proximal and distal end, attaching a resilient material at the distal end of the second elongate rod and manipulating the second elongate rod to position the resilient material at the distal end of the second elongate rod where desired in the vicinity of the cervix.

* * * * *